United States Patent [19]

Scanlon et al.

[11] Patent Number: 5,335,775
[45] Date of Patent: Aug. 9, 1994

[54] SUTURE DISPLAY RACK AND PROCEDURE KIT

[75] Inventors: Christopher Scanlon, Milford; David L. Brown, Wallingford, both of Conn.

[73] Assignee: United States Surgical Corporation, Norwalk, Conn.

[21] Appl. No.: 958,982

[22] Filed: Oct. 9, 1992

Related U.S. Application Data

[63] Continuation-in-part of Ser. No. 628,567, Dec. 17, 1990.

[51] Int. Cl.$^5$ .................. A61B 17/06; B65D 85/48
[52] U.S. Cl. .................. 206/63.3; 206/484.1; 206/453
[58] Field of Search .......... 206/63.3, 453, 586, 206/484.1, 425, 63.5

[56] References Cited

U.S. PATENT DOCUMENTS

| | | | |
|---|---|---|---|
| 1,217,243 | 2/1917 | Tucker et al. | 206/425 X |
| 1,977,466 | 10/1934 | Bohnke | |
| 2,034,116 | 3/1936 | Palen | |
| 2,476,102 | 7/1949 | Lobell | |
| 3,189,174 | 6/1965 | Cormack | 206/63.3 |
| 3,727,658 | 4/1973 | Eldridge, Jr. | 206/DIG. 33 |
| 3,759,376 | 9/1973 | Lisowski | 206/63.3 |
| 3,861,521 | 1/1975 | Burtz | 206/63.3 |
| 3,872,965 | 3/1975 | Taub | 206/44 |
| 4,000,811 | 1/1977 | Hardison et al. | 206/44 R |
| 4,063,638 | 12/1977 | Marwood | 206/63.3 |
| 4,210,239 | 7/1980 | Takahashi | 206/45.13 |
| 4,225,038 | 9/1980 | Egly | 206/45.18 |
| 4,249,656 | 2/1981 | Cerwin et al. | 206/63.3 |
| 4,253,563 | 3/1981 | Komarnycky | 206/63.3 |
| 4,260,056 | 12/1981 | Horvath et al. | 206/370 |
| 4,261,463 | 4/1981 | Shave | 206/63.3 |
| 4,651,872 | 3/1987 | Joyce | 206/45.14 |
| 4,730,725 | 3/1988 | Marshall, Sr. et al. | 206/63.3 |
| 4,781,292 | 11/1988 | Sacherman et al. | 206/425 X |
| 4,886,160 | 12/1989 | Kligerman | 206/44 R |
| 4,886,165 | 12/1989 | Annett | 206/370 |
| 4,936,314 | 6/1990 | Kasai et al. | 128/764 |
| 4,947,984 | 8/1990 | Kaufman et al. | 206/44.12 |
| 4,967,905 | 11/1990 | Steves | 206/453 X |
| 5,127,525 | 7/1992 | Hummer | 206/586 |
| 5,154,283 | 10/1992 | Brown | 206/63.3 |

FOREIGN PATENT DOCUMENTS

| | | | |
|---|---|---|---|
| 649011 | 10/1964 | Belgium | 206/63.3 |
| 635484 | 1/1962 | Canada | 206/63.3 |
| 1541150 | 2/1970 | Fed. Rep. of Germany | 206/63.3 |
| 2632849 | 12/1989 | France | 206/63.3 |

OTHER PUBLICATIONS

Publication entitled "Point of View", Ethican, Inc., vol. 25, No. 1, dated 1988.

*Primary Examiner*—Paul T. Sewell
*Assistant Examiner*—BethAnne C. Cicconi

[57] ABSTRACT

A suture display rack and procedure kit is provided which, upon folding, presents a plurality of stacked suture packages for seriatim review. The suture display rack is a substantially U-shaped structure with a floor portion and two opposing sidewall portions. A longitudinal fold line is provided in the floor portion parallel to the planes formed by the side walls such that, upon folding, the side wall portions may be brought into the same horizontal plane to form the base for the suture display rack. The suture packages may be loosely held in the rack or alternatively hinged to a side wall or contained in sheaths for ease of review and removal. The sheaths and suture packages can be sterilized separately from the display rack. The suture display rack may be securely adhered to a desired surface or may be set up in a portable manner.

5 Claims, 14 Drawing Sheets

SUTURE DISPLAY RACK AND PROCEDURE KIT

This is a continuation-in-part of copending application Ser. No. 07/628,567 filed Dec. 17, 1990.

BACKGROUND OF THE INVENTION

1. Field of the Invention

The present invention relates to storage and packaging of surgical devices and more particularly, to a prepackaged folding display rack and procedure kit for organized storage and presentation of sutures and the like.

2. Description of Related Art

Modern surgical procedures draw upon a wide variety of types and sizes of sutures. These sutures are usually contained in individual retainers or foil laminate envelopes wherein the suture is wound in a FIG. 8 pattern on a paper retainer as shown for example in U.S. Pat. Nos. 4,249,656, 4,253,563 and 4,063,638. The size and type of the suture is typically printed on the enclosure envelopes for ease of identification.

Depending upon the type of surgical procedure to be performed, a wide selection of sutures of different types and sizes must be available and readily accessible to the surgical staff. Currently, a large supply of different types and sizes of individually packaged sterilized sutures are maintained in the operating area. The packages are typically arranged in loose stacks according to type and size in an area adjacent the surgical instruments. However, these loose stacks have a tendency to become mixed and disorganized during surgery, particularly extended surgery, making it difficult and time consuming to locate the proper suture package with the type and size of suture required by the surgeon.

Similarly, a large number of used needles accumulate and are loosely kept in a separate location so that a needle count may be conducted once the surgery is completed. Structure for retaining used needles is discussed in U.S. Pat. No. 3,861,521 to Burtz wherein a disposable suture organizer is shown which incorporates a plurality of integral magnetic bars on each organizer.

Therefore, it would be highly desirable to have a suture display rack and procedure kit which contains a plurality of foldable suture packages in an organized presentation for ease of location and removal as needed.

Accordingly, it is one object of the present invention to provide a folding suture display rack and procedure kit for storing and displaying a plurality of suture packages organized for ease of reference and removal.

It is another object of the present invention to provide a suture display rack and procedure kit for storing and displaying a plurality of suture packages which rack is sterilizable as a single unit.

It is yet another object of the present invention to provide a plurality of pocketed sheaths having various combinations of suture packages disposed in the pockets wherein the sheaths and suture packages are sterilizable in breather pouches.

It is yet another object of the present invention to provide a protective shielding member to prevent a sheath from piercing or puncturing a surrounding breather pouch during sterilization or movement of the sheath and pouch.

It is a further object of the present invention to provide an inexpensive and convenient suture display rack and procedure kit for storing and displaying a plurality of suture packages which rack folds to present the suture packages in an organized manner and can be affixed in a predetermined convenient location.

It is another object of the present invention to provide a suture display rack and procedure kit for storing and displaying a plurality of suture packages which kit further provides means for assisting in the retention and counting of used needles.

These and other highly desirable and unusual results are accomplished by the present invention in a folding suture display rack and procedure kit for storing and displaying a plurality of suture packages interleaved to allow the user to easily and efficiently locate a desired suture type or size.

Objects and advantages of the invention are set forth in part herein and in part will be obvious therefrom, or may be learned by practice with the invention, which is realized and attained by means of the instrumentalities and combinations pointed out in the appended claims. The invention comprises novel parts, constructions, arrangements, combinations, steps and improvements herein shown and described.

SUMMARY OF THE INVENTION

According to the present invention, a foldable suture display rack and procedure kit is provided for storing and displaying a plurality of items such as, for example, suture packages such that, upon folding the suture packages are displayed in stacked sequential relation to facilitate seriatim review. The suture packages may be loosely stacked within the rack or releasably hinged to a sidewall thereof to maintain the order. Alternatively, a plurality of sheaths may be provided to hold the suture packages in place and facilitate easy removal. The suture display rack may be formed in a wide variety of sizes to contain a plurality of suture packages in different configurations. For example, a plurality of packages of a single size and type of suture can be individually packaged in stacked relation or, alternatively, a variety of sizes and types of sutures keyed to a given surgical procedure can be prepackaged in a single sterile package.

In the unfolded position the suture rack acts as a retainer for a plurality of suture packages and preferably may be sterilized as a single unit using, for example, conventional Tyvek® covered trays or enclosures. Preferably, the suture packages are presented slightly angled away from the viewer and oriented to display identifying indicia on the suture packages. In this manner, the viewer may simply flip through the suture packages to locate a desired size. For easier review and identification, organizer tabs may be used to subdivide the different sutures. An integral magnet bar also may be included to assist in retaining and accounting for used needles.

In one configuration, the unfolded structure of the suture display rack and procedure kit comprises a substantially U-shaped container having a horizontal floor portion and a pair of parallel or diverging opposing side walls. The horizontal floor portion is provided with a longitudinal fold line parallel to the planes formed by the side walls. The unfolded suture display rack and procedure kit has a plurality of suture packages disposed therein in stacked relation. In preferred embodiments, the suture packages are removably attached to a sidewall thereof either by hinges or plastic sheaths. The entire rack is preferably prepackaged and stored in a sterilizable tray prior to use. Alternatively, the plastic sheaths can be separately loaded with suture packages and sterilized independently from the display rack. The sheaths containing the suture packages may then be inserted into the display rack prior to use. In preparing for a surgical procedure, the unfolded suture display rack in accordance with this configuration is removed from its package and folded along the longitudinal fold line until the opposed side walls are horizontally disposed forming a base for the rack. The individual suture packages are thus presented in an organized fashion for seriatim review. In a preferred embodiment, side walls of the U-shaped container are angled vertically outward from each other such that, upon folding, the floor portion forms a triangular structure and the stacked suture packages are angularly presented for easier review.

The suture rack can be maintained in its folded position by locking means. Alternatively, adhering means positioned on an outside surface of the vertical walls may be used. When folded, these adhering means serve to anchor the vertical walls to the surface on which the suture display rack is to be positioned.

In another configuration, the unfolded structure of the suture display rack and procedure kit comprises a two level container with a horizontal floor portion, a pair of parallel or diverging opposing side walls and a pair of alignment walls adjacent each side wall. A plurality of suture package retainers are pivotally mounted proximate each of the opposing side walls in substantially horizontal stacked sequential relation forming at least two vertical containment levels.

A first level comprises the area defined by the floor portion, one side wall and an adjacent pair of alignment walls. The second containment level comprises the area defined by the opposite side wall, an adjacent pair of alignment walls and a substantially horizontal support element which projects from the side wall such that the second level is disposed at least partially above the first level.

In a preferred embodiment, the suture package retainers are angularly oriented with respect to the side walls so as to present the retained suture packages in better form for review when the kit is folded. The packages in the containment levels may be displayed in either substantially parallel or opposed planes as desired.

This configuration of the suture display rack folds and assembles in substantially the same way as the configuration discussed above. After removal from its packaging, the rack is folded along a longitudinal fold line until the side walls are substantially horizontally disposed forming a base for the rack. The suture package retainers in the first and second levels are preferably angularly oriented to facilitate seriatim review of sutures in either the first or second levels.

The rack is maintained in its folded position by locking means or adhering means including integral hinges, locking flaps, two way tape or other known fastening means.

BRIEF DESCRIPTION OF THE DRAWINGS

The accompanying drawings, referred to herein and constituting a part hereof, illustrate the preferred embodiments of the present invention, and, together with the description serve to explain the principles of the invention.

DETAILED DESCRIPTION OF THE PREFERRED EMBODIMENTS

Figure 1:
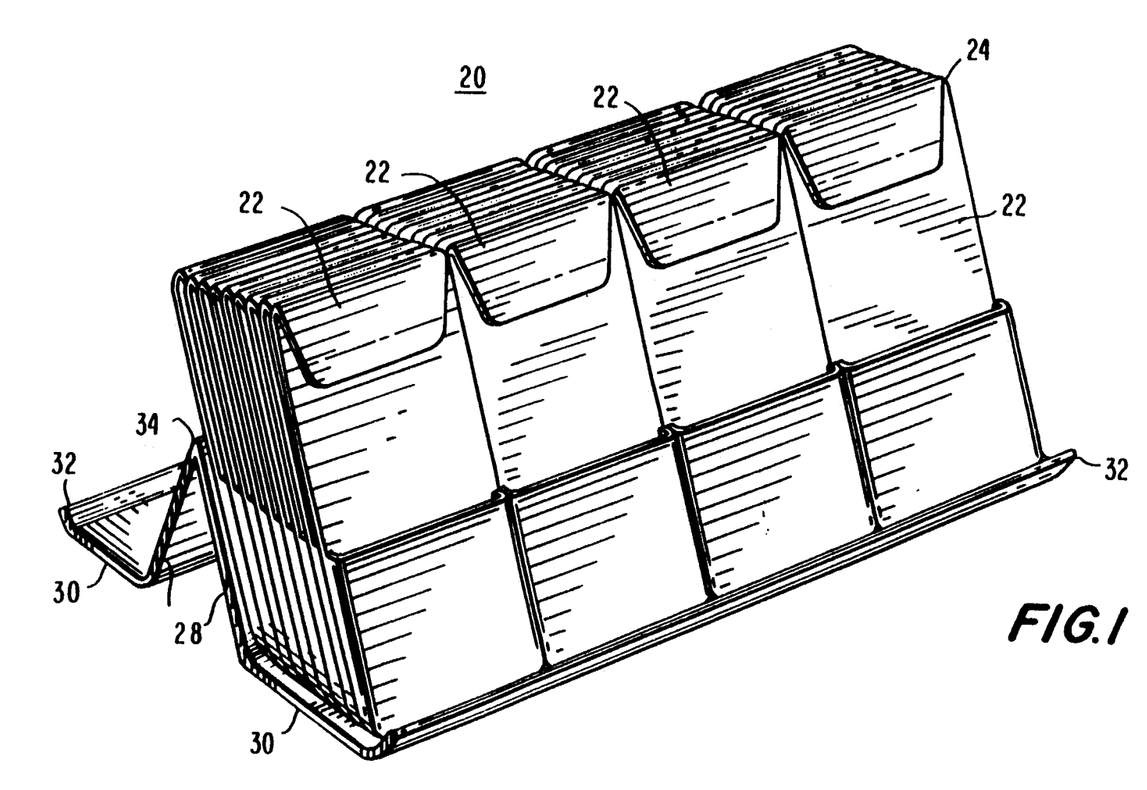
FIG. 1 is a perspective view of a suture display rack in accordance with one embodiment of the present invention.

Referring now to the figures and, in particular to FIG. 1, there is shown a suture display rack 20 in accordance with a preferred embodiment of the present invention. The suture display rack 20 contains a plurality of suture packages 22 serially stacked for easy access and review. In the embodiment of FIG. 1, suture packages 22 are arranged in sheets 24 of four suture packages in side by side configuration. Other arrangements are contemplated depending upon the surgical procedure, the packaging size, etc. The sheets 24 are presented to the user in angular form for ease of review of the individual suture packages.

Figure 2:
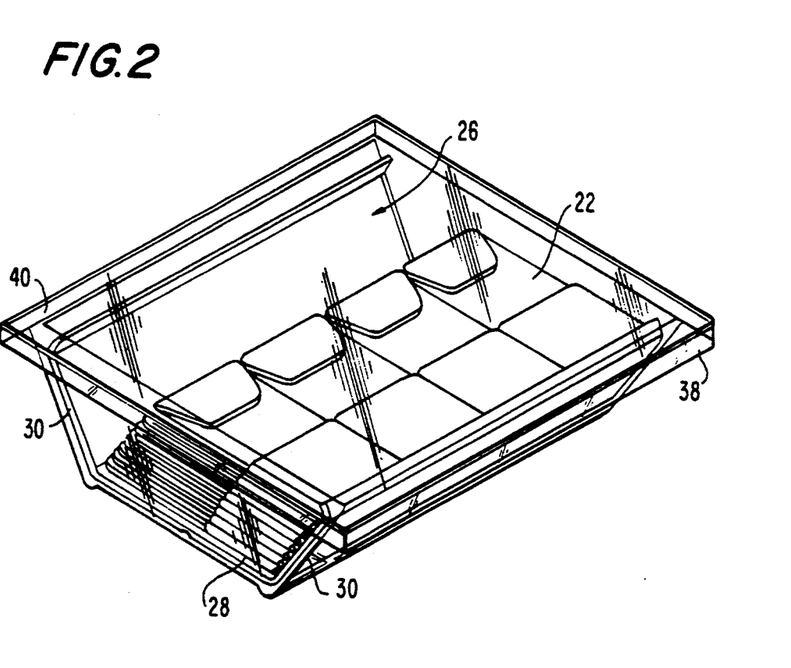
FIGS. 2-5 show the sequential opening and set up of a suture display rack in accordance with one embodiment of the present invention.
Figure 2A:
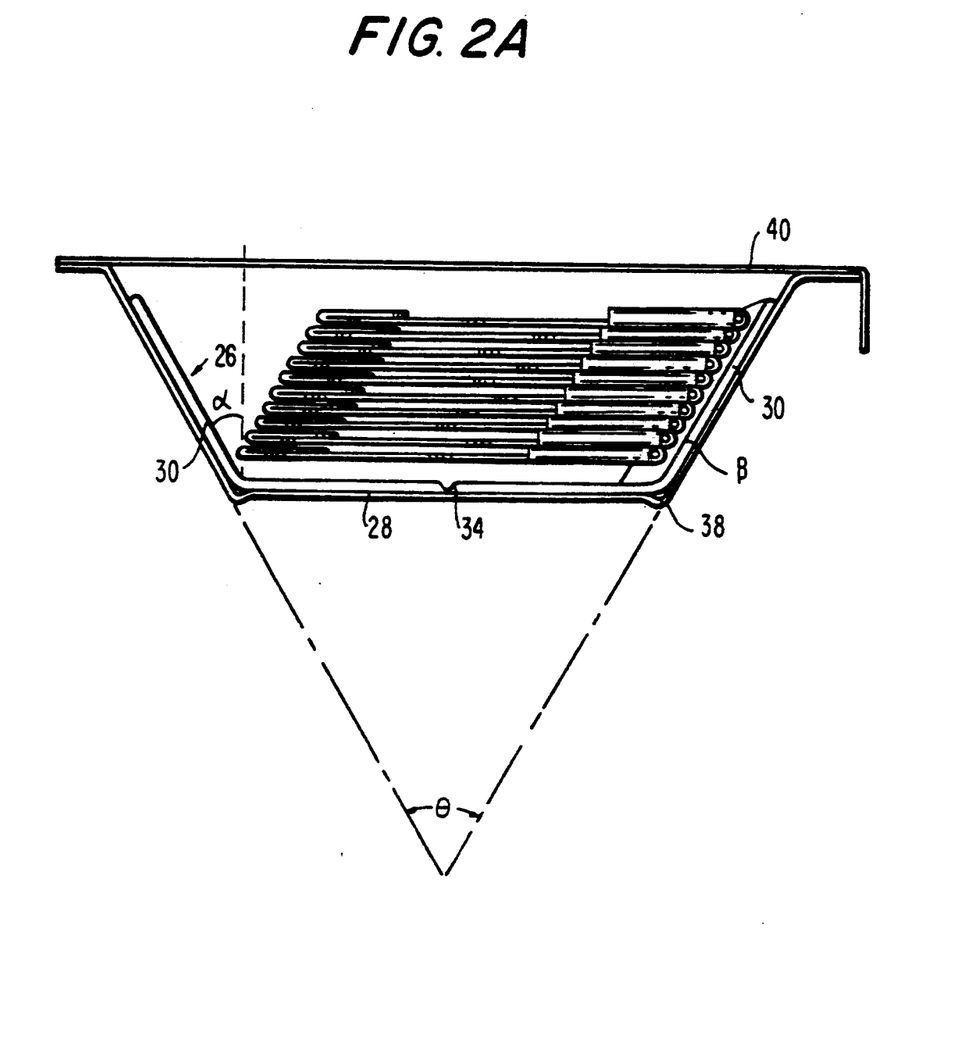
Figure 3:
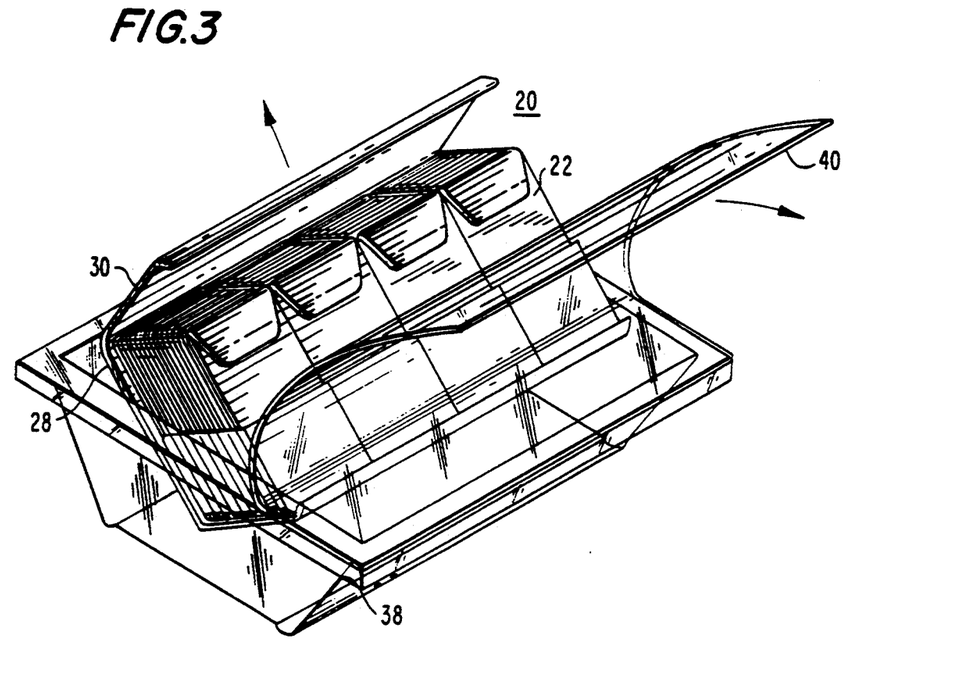
Figure 4:
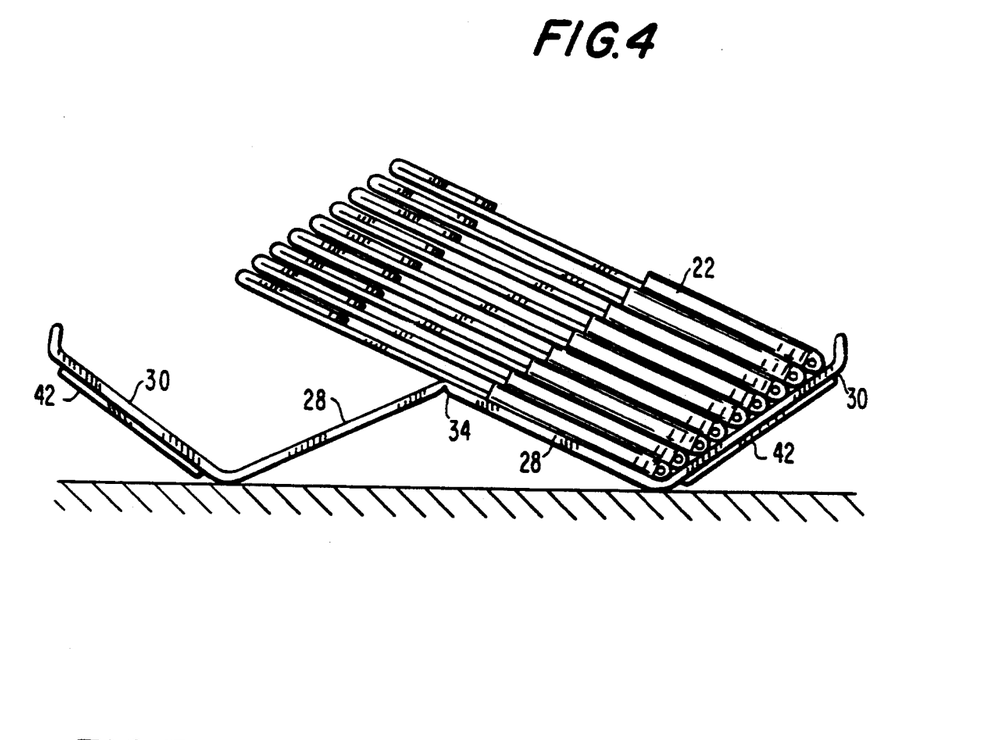

In the unfolded configuration, best seen in FIGS. 2-2A, the suture display rack comprises a substantially U-shaped container 26 having a horizontal floor portion 28 and two outwardly diverging side wall portions 30. In a preferred embodiment shown in FIG. 1, wherein suture packages are loosely stacked within the suture display rack, an inwardly converging flange portion 32 is formed at an end of the side wall portion 30 in order to prevent the stacked suture packages from sliding out and to maintain them in alignment when the suture display rack is set up. Alternatively, the suture packages may be removably hinged to one of the diverging side wall portions as shown in FIGS. 2-5. Sheaths 36 (FIG. 6) also may be rotatably fixed to one of the diverging side walls to hold individual suture packages. These sheaths may be formed of a transparent or translucent plastic or paper material and may be color coded as desired. Where either of these two alternate embodiments are used, the flange portion 32 may be eliminated.

A fold line 34 is formed longitudinally along the floor portion 28 parallel to the planes formed by side wall portions 30 to facilitate bending of the suture display rack 20. The storage rack is preferably formed from a moldable plastic material such as, for example, polyethylene terephthalate (PETG), Eastman Kodak 6763 or other suitable material.

During set up, the rack 20 is folded until the outwardly diverging side wall portions 30 are in substantially the same horizontal plane thus forming the floor portion 28 into a substantially triangular shape as shown in FIGS. 1 and 4–6. In this folded configuration, side wall portions 30 form a stable base for the suture display rack 20 and the folded floor portion serves to support and present the suture packages in an organized and easily reviewable angled format. It is readily apparent that the angled presentation of the suture packages is easily varied by increasing or decreasing the total angle of divergence T of side wall portions 30 within the range of 0° and 180°, with 0° representing parallel sidewalls and 180° representing sidewalls in the same horizontal plane (FIG. 2A). The total angle of divergence T represents the sum of the radial angles of divergence a and β of side walls 30 from a plane perpendicular to floor portion 28.

Referring to FIGS. 2–5, there is shown a sequential storage and set up of a suture display rack in accordance with another preferred embodiment of the present invention. The unfolded suture display rack 20, having a plurality of suture packages 22 removably hinged to side wall portion 30, is stored within a procedure tray 38. For convenience and ease of sterilization, the loaded suture display rack is sealed within the procedure tray 38 by a cover sheet 40 constructed of a material which is previous to ethylene oxide sterilizing gas. The preferred material is a spun bonded polyolefin fiber, such as Tyvek® 1073B available from E.I. DuPont de Nemours & Co.

Figure 5:
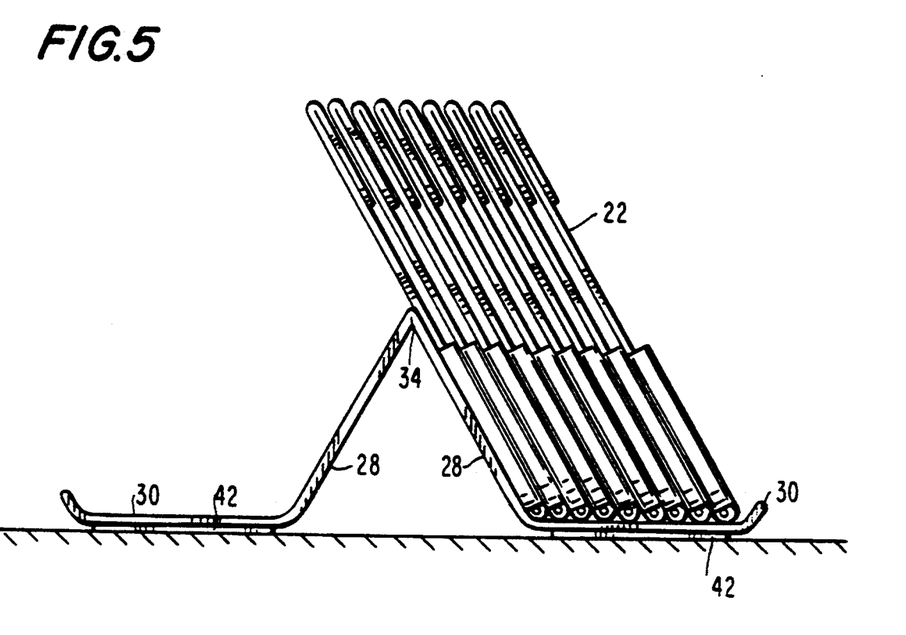
Figure 6:
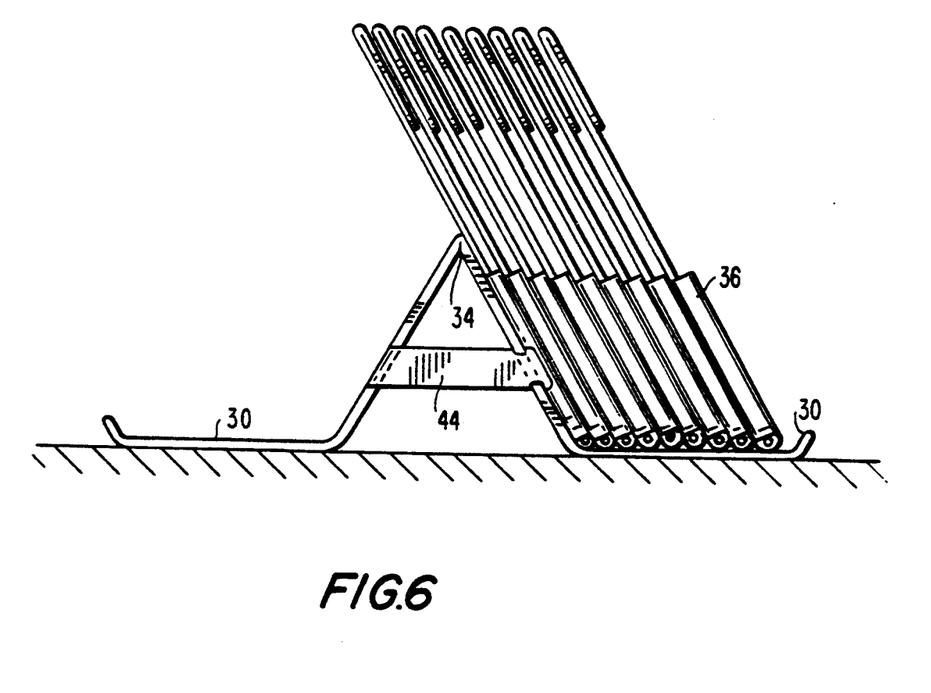
FIG. 6 is a side view of an alternate embodiment of the present invention wherein the suture display rack is maintained in a folded position by locking means.

Once the cover sheet 40 is peeled back, (FIG. 3) the suture display rack 20 is lifted out and moved to a preferably sterile field at a desired location in the operating room. The suture display rack is folded downwardly along fold line 34 (FIG. 4) until side walls 30 are in substantially the same horizontal plane. Adhering means, in this case two-way tape 42, is positioned on the outer side of side walls 30. When the desired location is selected, the backing of the tape 42 is removed and the suture display rack is firmly adhered (FIG. 5).

Alternatively, where a movable suture display rack is desired, locking means in the form of flap 44 (FIG. 6) is provided to interconnect and lock the opposing sides of the folded floor portion 28 to hold the suture display rack in fixed orientation without the need for adhering means to fix the side walls 30 to a mounting location. In this embodiment the folded suture display rack may be moved from one location to another.

Figure 7:
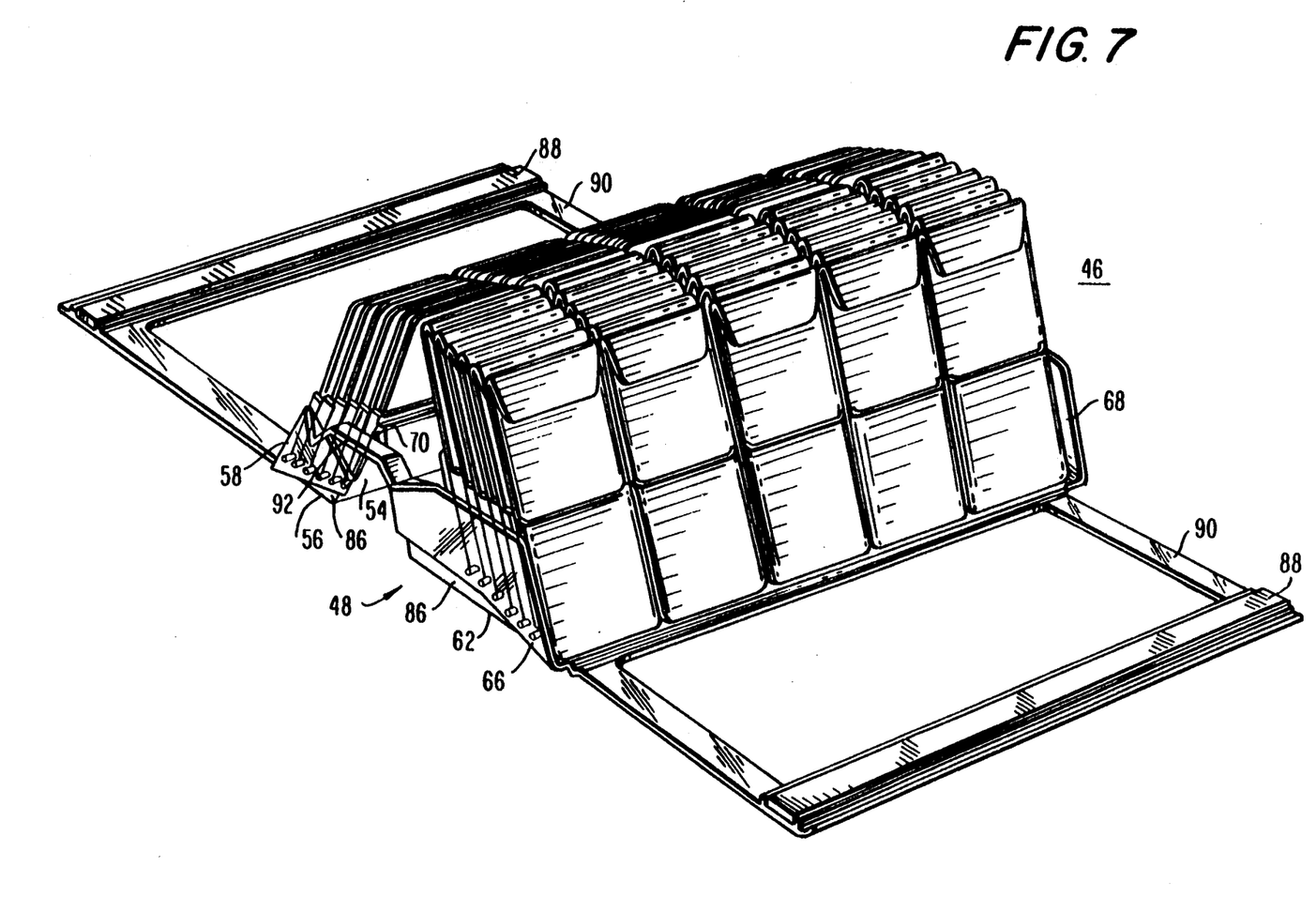
FIG. 7 is a perspective view of another preferred embodiment of the present invention wherein the suture rack has two opposed suture containment levels.
Figure 8:
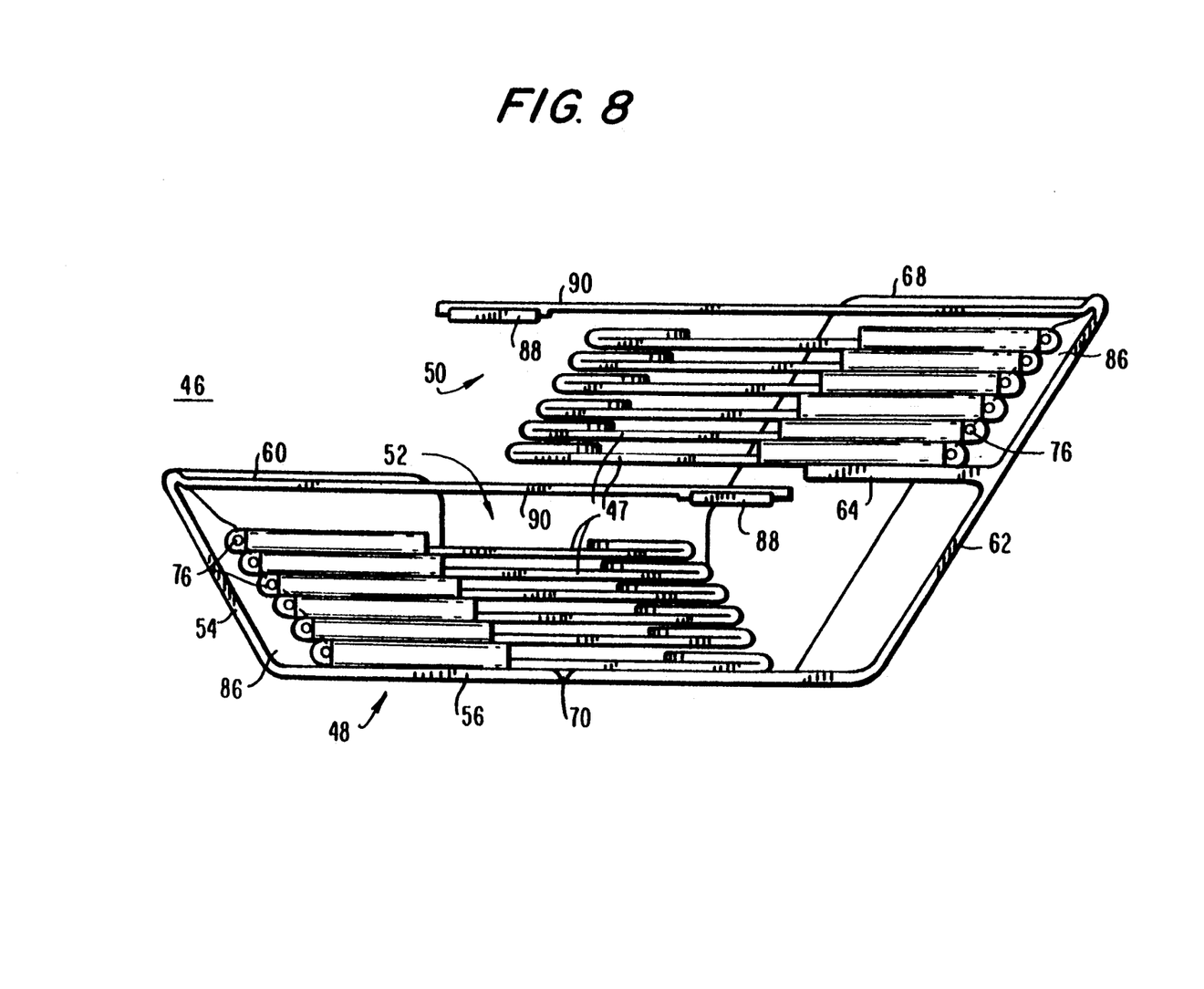
FIG. 8 is a side view in cross-section of the embodiment of FIG. 7 in the unfolded position.
Figure 9:
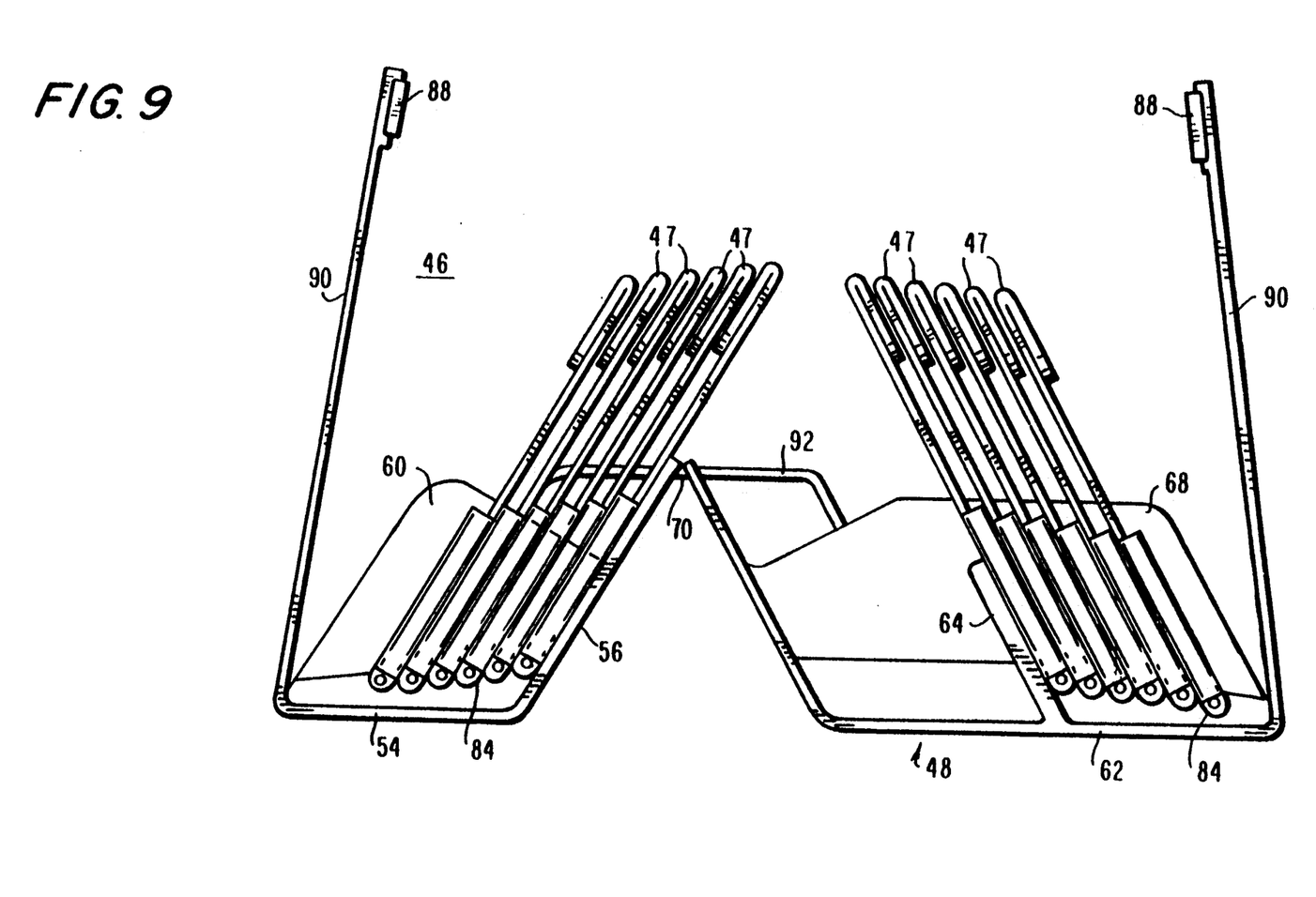
FIG. 9 is a side view in cross-section of the embodiment of FIG. 7 in the folded position.

Referring to FIGS. 7–9, another preferred embodiment of the suture display rack 46 is shown having an expanded capacity for storing and displaying suture packages 47 in two suture containment levels. In the unfolded configuration, best seen in FIG. 8, the suture display rack 46 comprises a container 48 having an upper containment level 50 and a lower containment level 52 formed therein.

Lower containment level 52 is at least partially defined by sidewall 54, floor portion 56 and alignment walls 58 and 60. Upper containment level 50 is disposed above lower containment level 52 and is at least partially defined by sidewall 62, support projection 64 and alignment walls 66 and 68.

As in previous embodiments, a fold line 70 is provided in floor portion 56 allowing sidewalls 54 and 62 to pivot. Sidewalls 54 and 62 are preferably formed in a diverging configuration and, together, act as a base for the display rack 46 in its folded position. See FIGS. 7 and 9.

Figure 10:
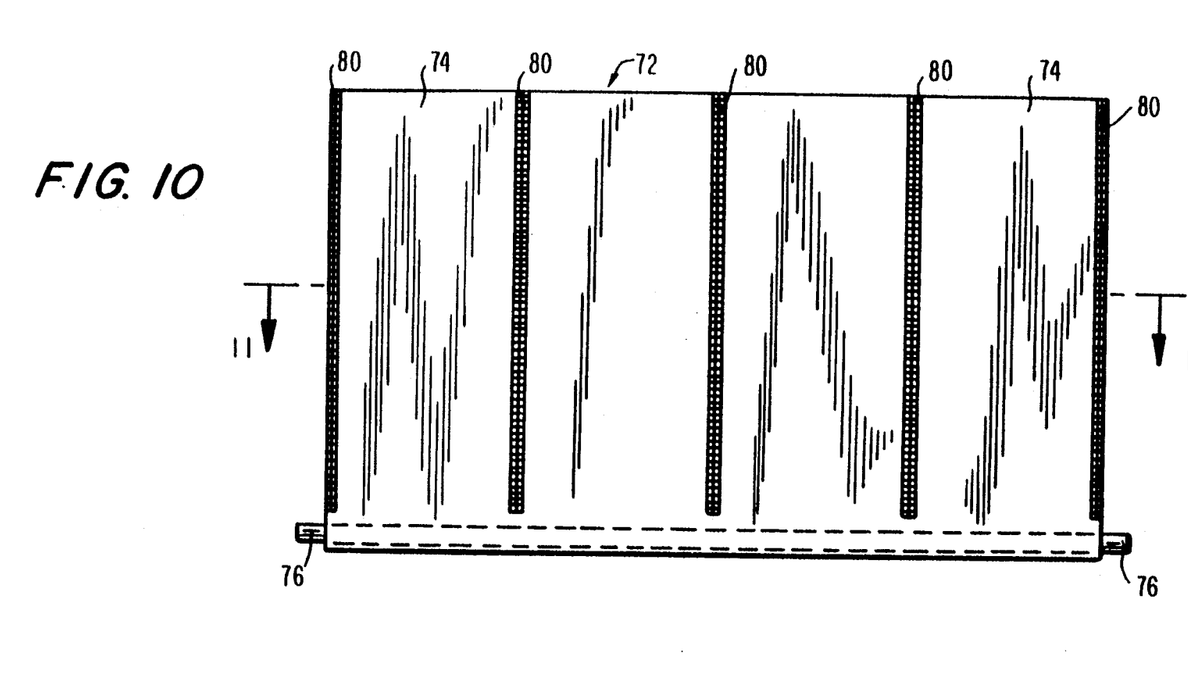
FIG. 10 is a frontal view of the plastic sheaths in accordance with one embodiment of the present invention.
Figure 11:
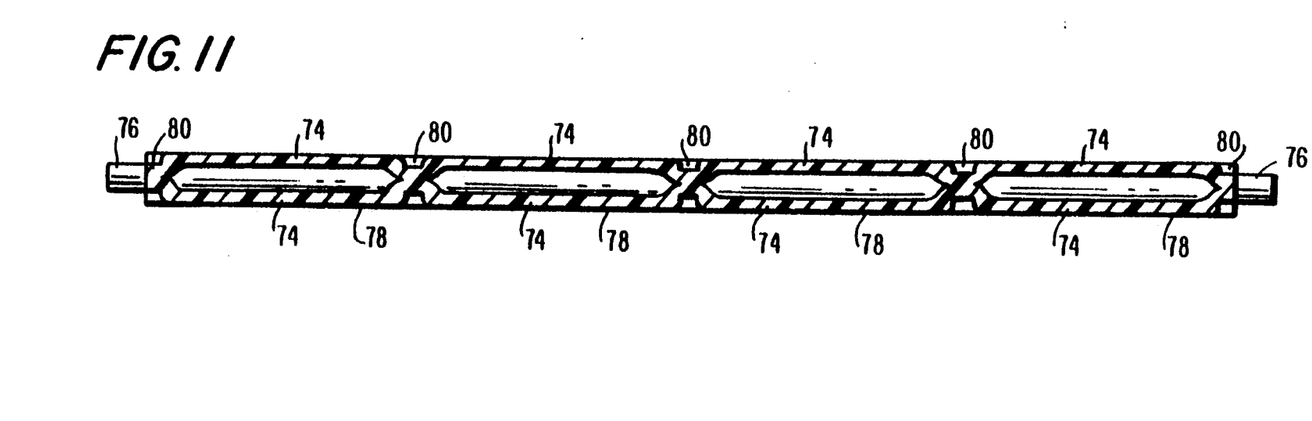
FIG. 11 is a top cross-sectional view taken along line 11—11 in FIG. 10 of the plastic sheaths.

A plurality of sheaths 72 are flexibly mounted in both upper and lower containment levels 50 and 52 in a substantially stacked horizontal configuration to facilitate efficient storage. Referring to FIGS. 10–11, there is shown a preferred embodiment of the sheath 72 in accordance with the present invention. The sheath 72 comprises an elongated sheet of retaining material 74, such as for example, paper, plastic, especially heat sealable plastic, etc., which is folded in half around shaft 76 and bonded to form retaining portions 78 therein. In the embodiment shown in FIGS. 10–11, the retaining material 74 is a heat sealable plastic and retaining portions or pockets 78 are formed by heat sealing opposing faces of the retaining material 74 along lines 80 substantially perpendicular to shaft 76. Alternatively, with reference to FIG. 15, sheath 72' can be fabricated from retaining material 74 which is cut and folded to form integral protrusions 77A and 77B. Heat sealing along line 81 provides sufficient structural integrity such that shaft 76 (see, e.g., FIG. 10) may be omitted. Using either of these fabrication methods, sheaths 72 and 72' can be efficiently and economically produced.

Figure 12:
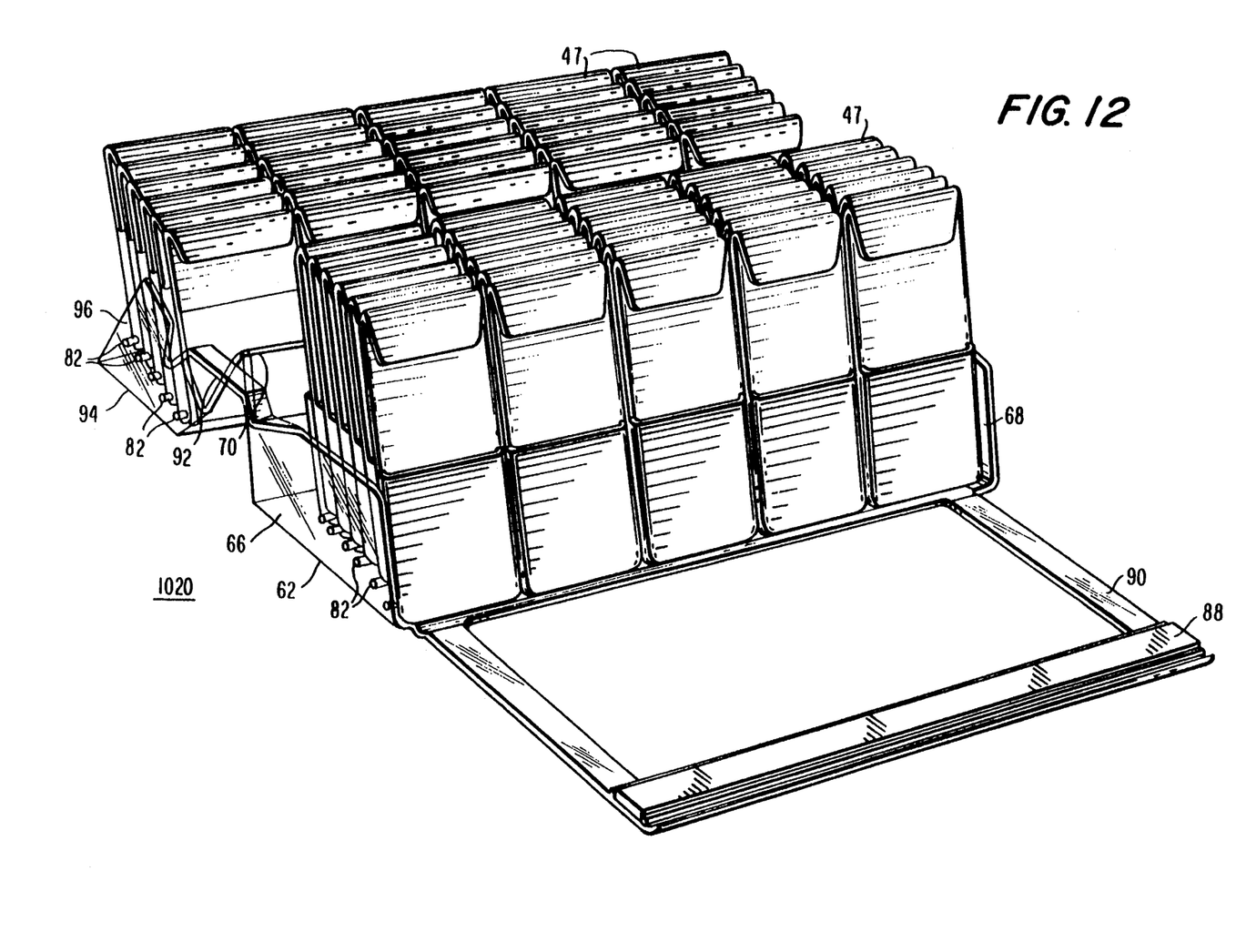
FIG. 12 is a perspective view of another preferred embodiment of the present invention wherein the suture packages in the two suture containment levels are presented in substantially parallel planes.
Figure 13:
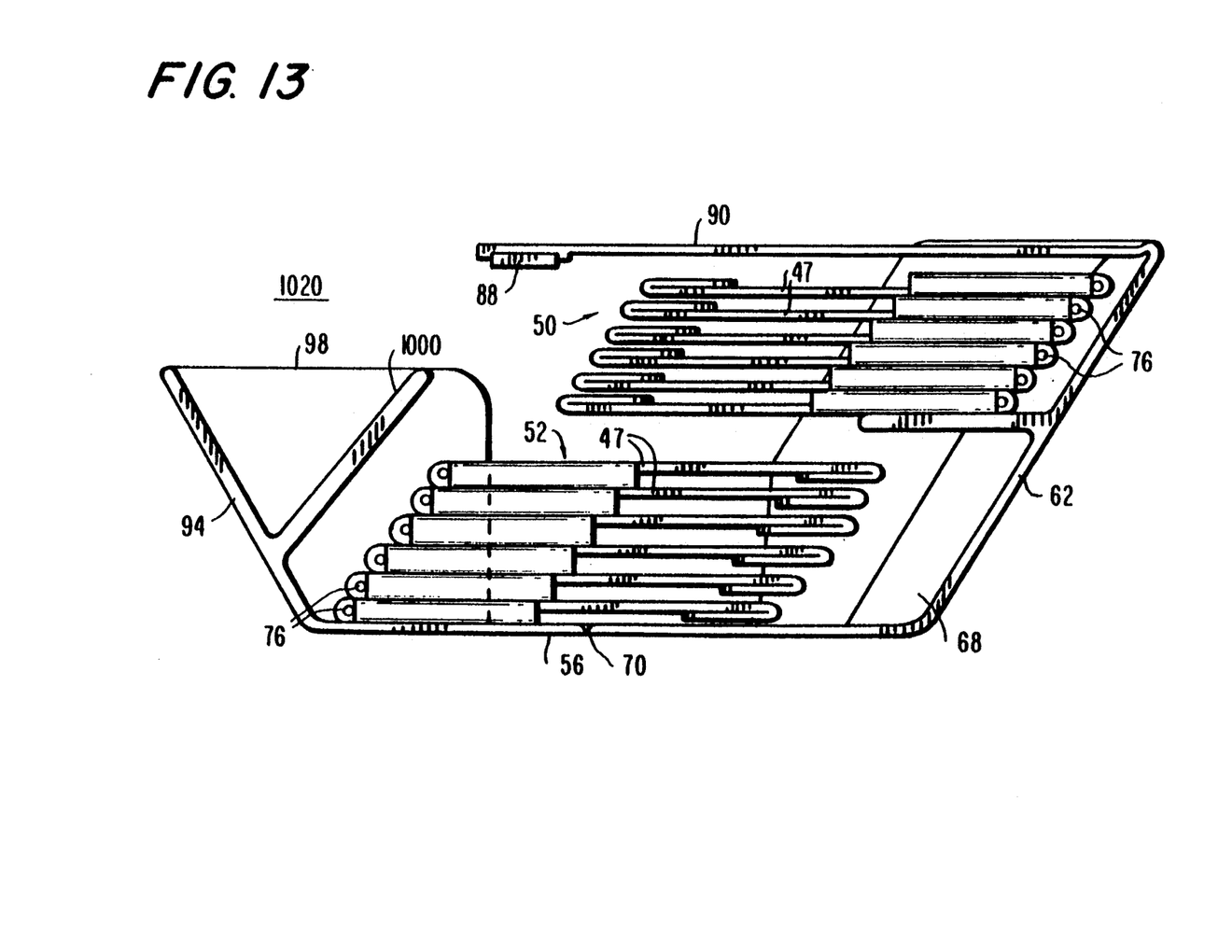
FIG. 13 is a side view in cross-section of the embodiment of FIG. 12 in the unfolded position.
Figure 14:
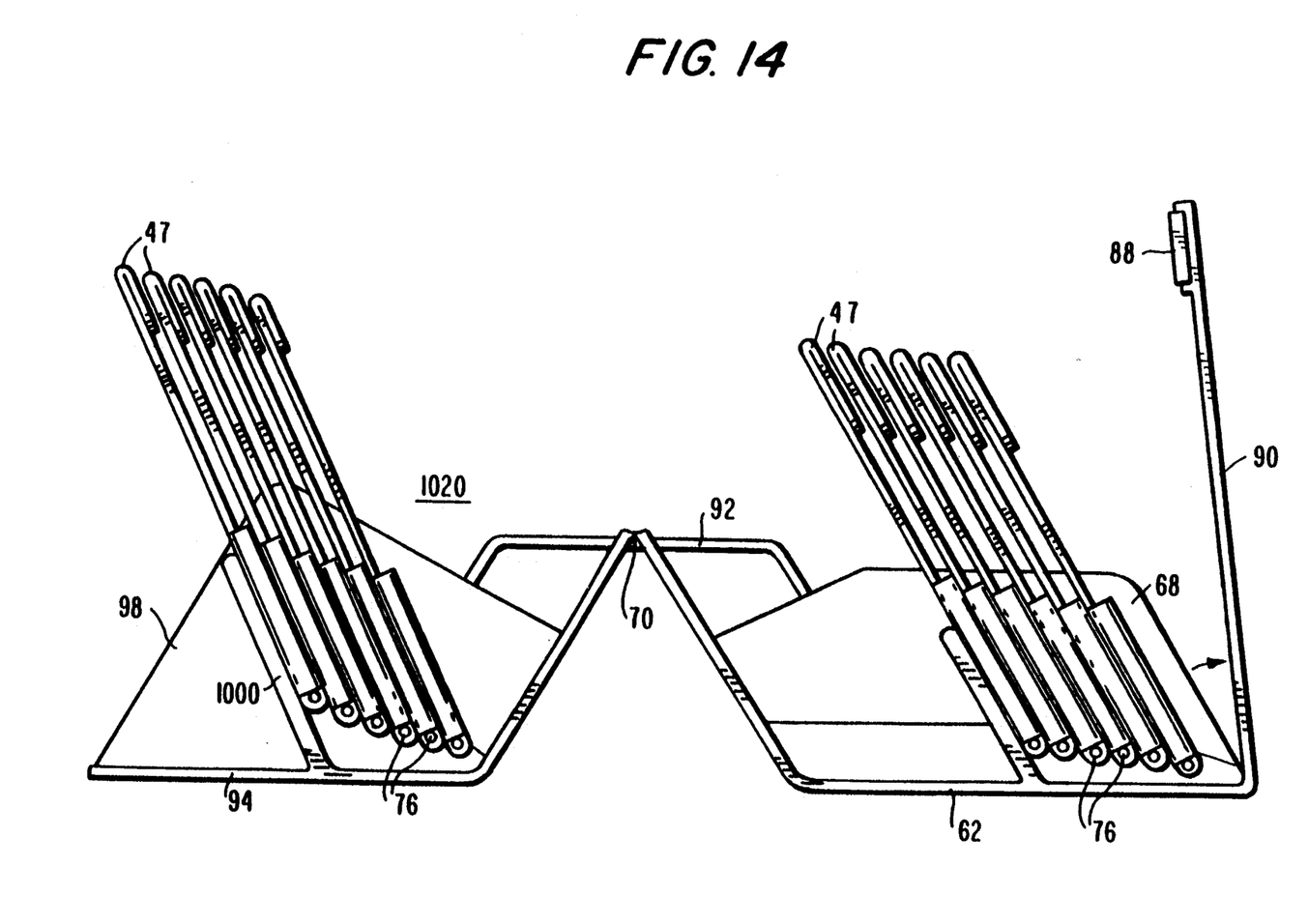
FIG. 14 is a side view in cross-section of the embodiment of FIG. 13 in the folded position.
Figure 15:
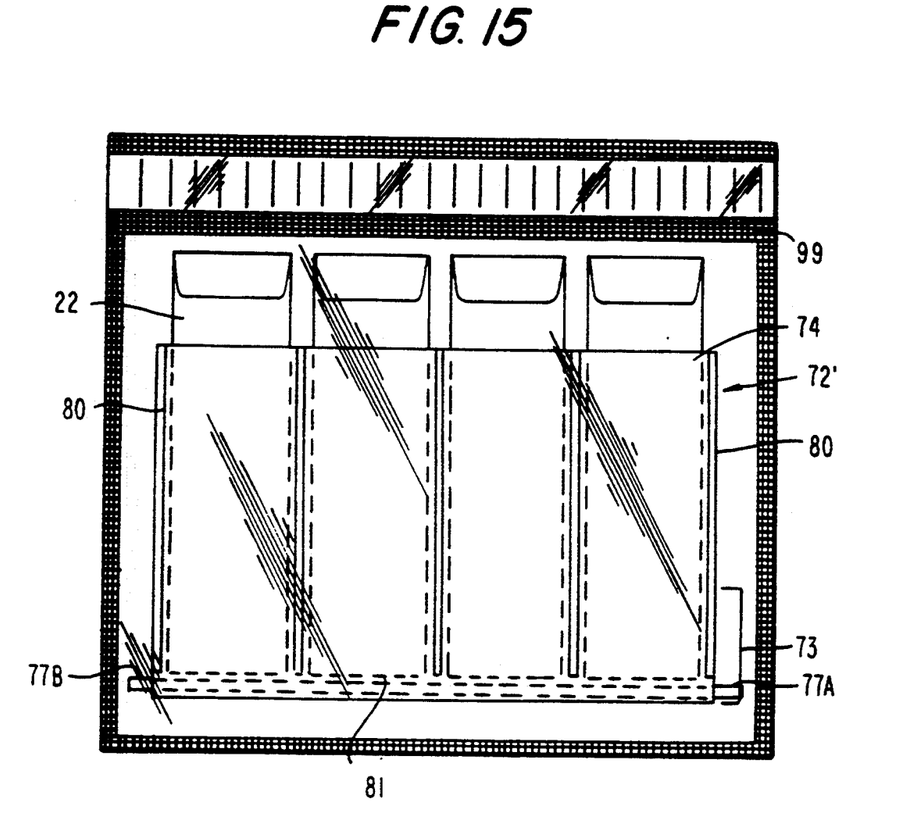
FIG. 15 is a frontal view of an alternative embodiment of the plastic sheaths containing suture packages and disposed within a breather pouch.

Sheaths 72 may be mounted within upper and/or lower containment levels 50 and 52 using a variety of methods. As shown in FIGS. 12, 13 and 14, shafts 76 of sheaths 72 are inserted into bores 82 formed in alignment walls 58, 60, 66 and 68 respectively. Alternatively, snap fit clips 84 may be formed in either the sidewalls 54 and 62 or alignment walls 58, 60, 66 and 68 to receive and retain shafts 76 of sheaths 72. These clips 84 may be disposed on separate shelf structure 86 within the upper and lower containment levels 50 and 52 where desired. In an alternative embodiment, protrusions 77A and 77B, as illustrated in FIG. 15, can function in a manner similar to shaft 76.

Magnet bars 88 may be included as part of suture display rack 46 and are adapted to hold metallic elements such as, for example, used needles, clips, staples, etc. to facilitate accounting for such elements after surgery is completed. In the embodiment shown in FIGS. 7–9, a magnet bar 88 is mounted on folding support structure 90 attached to sidewalls 54 and 62. In the unfolded position (FIG. 8) support structure 90 is disposed over adjacent containment levels 50 and 52 and is substantially parallel to suture packages 47 in sheaths 72 for efficient storage. Upon folding (FIGS. 7 and 9) the support structure 90 pivots respectively about sidewalls 54 and 62 and lays flat on the supporting surface in the same horizontal plane as sidewalls 54 and 62. In this position magnet bars 88 are presented for receiving and retaining metallic elements.

In order to deploy this embodiment of the suture display rack into the folded position (FIG. 7), both sidewalls 54 and 62 are grasped and pivoted downward about fold line 70. When both sidewalls 54 and 62 are in substantially the same horizontal plane, locking means are employed to maintain the rack in the folded position. In the embodiment shown in FIGS. 7–9, an over-center hinge 92 is provided adjacent to and transverse of fold line 70. This hinge 92 is flexibly attached to alignment walls 58 and 66 and is adapted to flex to allow folding of sidewalls 54 and 62 and the thereafter maintain sufficient tension on alignment walls 58 and 66 to maintain the rack 46 in the folded position.

Referring now to FIGS. 12–14, there is presented another preferred embodiment of the present invention. The embodiment of FIGS. 12–14 is substantially the same as that shown and described above with respect to FIGS. 7–9 with the exception that the suture packages 47 disposed in lower containment level 52 are adapted to be displayed in a plane substantially parallel to the display plane of the suture packages in upper containment level 50 and only a single magnet bar is used. This display orientation is accomplished in the present embodiment by lengthening sidewall 94 and providing enlarged alignment walls 96 and 98 adjacent sidewall 94. Support structure 1000 is added to support the suture packages when the rack 1020 is folded.

Sheaths 72 are positioned in bores 82 formed in alignment walls 96, 98, 66 and 68 respectively to receive shafts 76 therein. Upon deployment to the folded position (FIG. 12) the suture packages 47 in lower containment level 52 are simply pivoted back about shafts 76 against support structure 1000 to orient those packages in a plane substantially parallel to the display plane of the packages in the upper containment level.

As in previously described embodiments, an overcenter hinge 92 is used as the locking means to maintain sidewalls 94 and 62 in the desired base portion. Alternatively, other locking or adhering means may be employed to maintain the display rack in the folded position including, but not limited to, two-way tape, locking tabs, etc.

Figure 16:
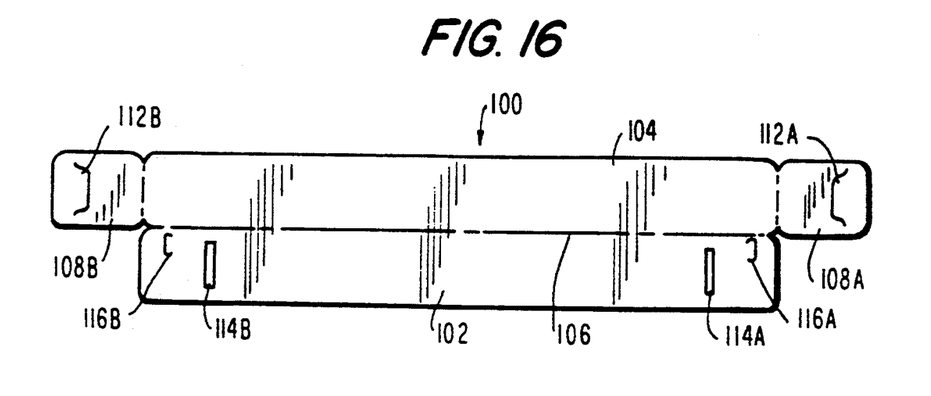
FIG. 16 is a top view of an unfolded plastic sheath cover in accordance with the present invention.
Figure 17:
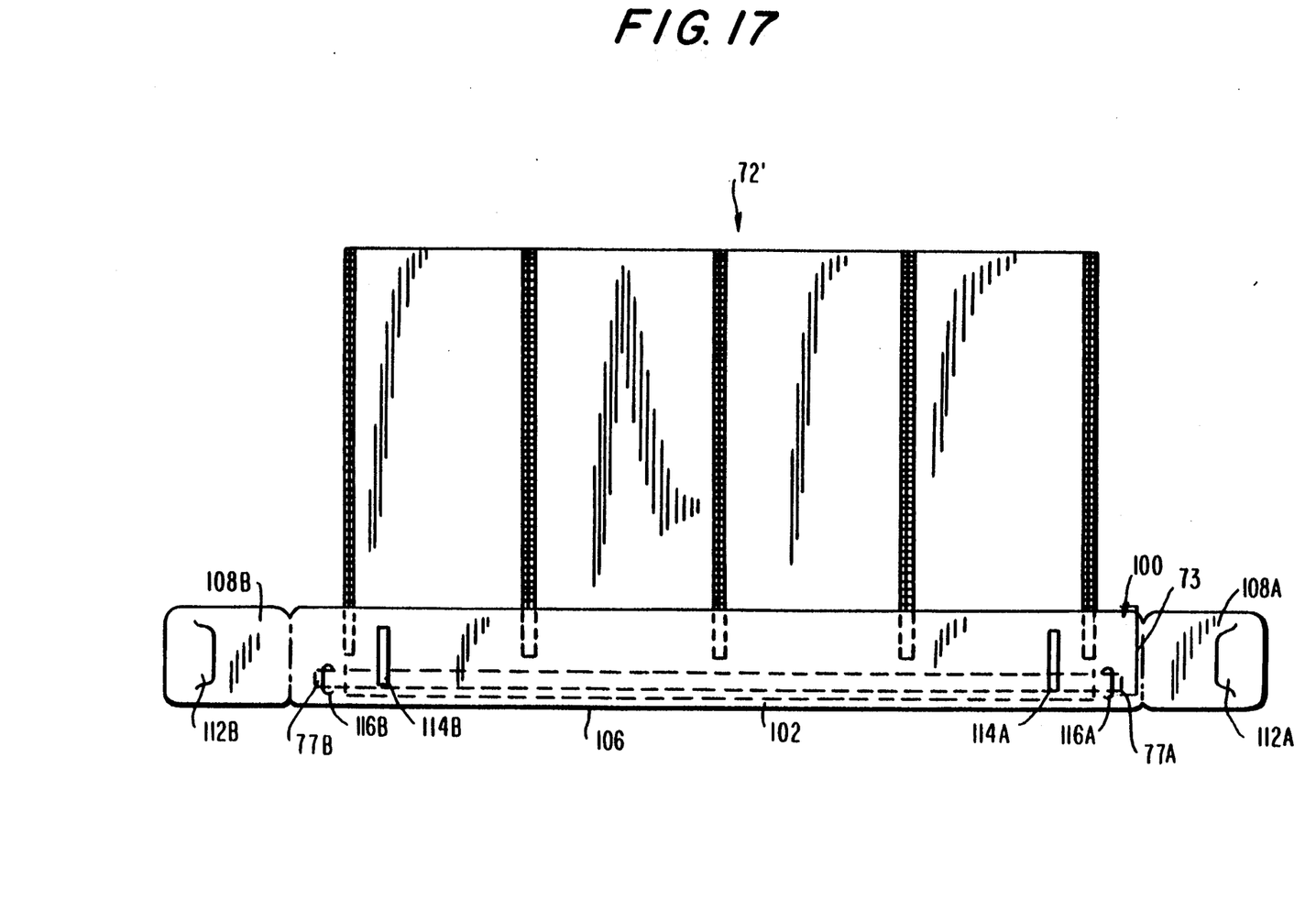
FIG. 17 illustrates a frontal view of the sheath cover of FIG. 16 partially folded about the plastic sheath of FIG. 15.

In an alternative method of packaging and sterilizing, with reference to FIGS. 15–17, sheath 72' is loaded with suture packages 22, enclosed in a sealed pouch 99 and sterilized as a single unit. Preferably, pouch 99 is at least partially constructed of a gas permeable material such as, for example, Tyvek®. These units can then be opened and placed in a display rack prior to use. In a preferred embodiment, a protective shielding member is disposed about a lower portion 73 of sheath 72' to ensure that protrusions 77A and 77B (or shaft 76 in FIG. 10) do not pierce pouch 99 during sterilization or transportation.

To accommodate this need, a sheath cover 100, shown in FIG. 16, is provided. Sheath cover 100 is formed of a plurality of interconnected panels, and in the preferred embodiment comprises two panels which are foldable over each other through a series of scored or perforated fold lines.

Referring to FIG. 16, a first panel 102 serves as a front cover panel. Panel 102 is connected to the second, back panel 104 along fold line 106. Side closure flaps 108A and 108B are connected to panel 104 along fold lines 110A and 110B, respectively. Flaps 108A and 108B have locking tabs 112A and 112B which are configured and dimensioned to engage slots 114A and 114B on panel 102, respectively. Panel 102 is dimensioned such that the ends of shaft 76 or protrusions 77A and 77B do not extend beyond panel 102. Thus, side closure flaps 108A and 108B fold over the ends or protrusions to enclose and prevent them from directly engaging the outer packaging. As best seen in FIG. 17, panel 102 also has slits 116A and 116B which permit sheath protrusions 77A and 77B to be passed therethrough. These slits 116A and 116B serve to anchor and engage the shielding member to the sheath and prevent shifting and disengagement thereof during shipping.

FIG. 17 illustrates a partial assembly of sheath cover 100 wherein panels 102 and 104 are folded along fold line 106 and sheath 72' is disposed therebetween. Protrusions 77A and 77B pass through slits 116A and 116B, respectively but does not extend beyond the package. By folding side closure flaps 108A and 108B over panel 102 and inserting locking tabs 112A and 112B into slots 114A and 114B, respectively, flaps 108A and 108B will cover protrusions 77A and 77B and, therefore, protect any additional packaging (i.e. a Tyvek® breather pouch, as shown in FIG. 15) from puncture by protrusions 77A and 77B.

Sheath cover 100 can be fabricated from a variety of materials such as, for example, paper, paperboard, fiberboard, or Tyvek®. Preferably, 12–12 point solid bleached sulfate paperboard is used, such as that available from Manadnock Paper Mills, Inc., Bennington, N.H.

To the extent not already indicated, it also will be understood by those of ordinary skill in the art that any one of the various specific embodiments herein described and illustrated may be further modified to incorporate features shown in other of the specific embodiments.

The invention in it broader aspects therefore is not limited to the specific embodiments herein shown and described but departures may be made therefrom within the scope of the accompanying claims without departing from the principles of the invention and without sacrificing its chief advantages.

What is claimed is:

1. A sterilizable package for retaining surgical elements, said package comprising:
    a sheath member having at least one retaining portion formed therein, said sheath member configured to permit sterilization;
    at least one suture package disposed in said retaining portion of said sheath;
    a sealed pouch enclosing said sheath member having said at least one suture package disposed in said retaining portion thereof, said pouch including means for permitting sterilization of an interior of said pouch;
    shielding means disposed adjacent at least a portion of said sheath member for preventing direct engagement of said portion of said sheath member and said pouch, said shielding means comprising at least first and second interconnected panels disposed about a lower portion of said sheath, wherein said first panel comprises a front cover and said second panel comprises a back cover for receiving said lower portion of said sheath, wherein said first panel further comprises two slots formed adjacent opposing ends of said panel and said second panel further comprises two side closure flaps having locking tabs formed therein which are configured and dimensioned to engage said two slots.

2. The package according to claim 1, wherein said first and second panels are configured and dimensioned to be folded about a lower portion of said sheath.

3. A sterilizable package as in claim 1, wherein said sheath further comprises protrusions extending from a lower portion thereof.

4. The package according to claim 3 wherein said shielding means having said first panel further comprises at least two slits configured and dimensioned to receive said protrusions therethrough.

5. A method of displaying a plurality of suture packages in a sterile condition comprising:
- a) providing a sheath member having at least one retaining portion formed therein;
- b) loading at least one suture package into said at least one retaining portion of said sheath;
- c) disposing shielding structure about a lower portion of said sheath, said shielding structure having first and second interconnected panels, said first panel having two slots formed adjacent opposing ends of said panel and said second panel two side closure flaps having locking tabs formed therein, said locking tabs being adapted to engage the slots of said first panel;
- d) placing said sheath, said at least one suture package and said shielding structure into a sterilizable pouch;
- e) sterilizing said sheath, said at least one suture package and said shielding structure;
- f) removing said sterilized sheath, said at least one suture package and said shielding structure from said pouch;
- g) removing said shielding structure from said sheath; and
- h) placing said sheath and said at least one suture package into a suture display rack.

* * * * *